US011881317B2

(12) United States Patent
Ramalho et al.

(10) Patent No.: US 11,881,317 B2
(45) Date of Patent: Jan. 23, 2024

(54) SYSTEMS AND METHODS FOR USING ACOUSTIC COMMUNICATIONS FOR CONTACT TRACING WITHIN ADMINISTRATIVE BOUNDARIES

(71) Applicant: Michael A. Ramalho, Lakewood Ranch, FL (US)

(72) Inventors: Michael A Ramalho, Lakewood Ranch, FL (US); Gail W. Karaman, Lakewood Ranch, FL (US)

( * ) Notice: Subject to any disclaimer, the term of this patent is extended or adjusted under 35 U.S.C. 154(b) by 183 days.

(21) Appl. No.: 17/332,502

(22) Filed: May 27, 2021

(65) Prior Publication Data

US 2021/0375483 A1  Dec. 2, 2021

Related U.S. Application Data

(63) Continuation-in-part of application No. 17/325,921, filed on May 20, 2021.

(60) Provisional application No. 63/060,089, filed on Aug. 2, 2020, provisional application No. 63/032,587, filed on May 30, 2020.

(51) Int. Cl.
*G16H 50/80* (2018.01)
*H04B 11/00* (2006.01)

(52) U.S. Cl.
CPC ............. *G16H 50/80* (2018.01); *H04B 11/00* (2013.01)

(58) Field of Classification Search
CPC ......... G16H 50/80; G16H 40/67; H04B 11/00
See application file for complete search history.

(56) References Cited

U.S. PATENT DOCUMENTS

| | | | | |
|---|---|---|---|---|
| 2007/0222599 A1* | 9/2007 | Coveley | ................... | G07C 9/28 340/572.4 |
| 2011/0301439 A1* | 12/2011 | Albert | ................... | G16H 40/63 600/509 |
| 2014/0104059 A1* | 4/2014 | Tran | ................... | A61B 5/6891 340/539.12 |

OTHER PUBLICATIONS

Payne, "NOVID is the Most Accurate App for Contact Tracing", Carnegie Mellon University News, https://www.cmu.edu/news/stories/archives/2020/june/novid-update.html, Jun. 30, 2020, retrieved on May 19, 2021, 3 pages.

* cited by examiner

*Primary Examiner* — Daniel L Murphy
*Assistant Examiner* — Amie M Ndure
(74) *Attorney, Agent, or Firm* — Mooney IP

(57) ABSTRACT

Systems, computer-implemented methods, and non-transitory computer-readable media are provided for performing contact tracing using acoustic communications within or across administrative domains. A computer-implemented method may include obtaining information associated with one or more acoustic tokens from a first user device of a first user where the one or more acoustic tokens were broadcast from an emitter device in an acoustic volume via an audio communication channel, obtaining information associated with one or more acoustic tokens broadcast from the emitter device from a second user device of a second user, determining whether the second user was exposed to a disease associated with the first user in the acoustic volume based on analyzing the information associated with the acoustic tokens from the first user device and the information associated with the acoustic tokens from the second user device, and providing information indicating whether the second user was exposed to the disease.

19 Claims, 11 Drawing Sheets

Depiction of Acoustic Volumes

Depiction of Association
Within an Acoustic Volume

SYSTEMS AND METHODS FOR USING ACOUSTIC COMMUNICATIONS FOR CONTACT TRACING WITHIN ADMINISTRATIVE BOUNDARIES

CROSS-REFERENCE TO RELATED APPLICATIONS

The present application claims the benefit of U.S. Provisional Patent Application No. 63/032,587, which was filed May 30, 2020 and entitled "System and Method Using Acoustic Communications for Contact Tracing within Administrative Boundaries," claims the benefit of U.S. Provisional Patent Application No. 63/060,089, which was filed Aug. 2, 2020 and entitled "Simplified System and Method Using Acoustic Communications for Contact Tracing within Administrative Boundaries," which also claims priority to U.S. Provisional Patent Application No. 63/032,587, which was filed May 30, 2020, and is a continuation-in-part of U.S. patent application Ser. No. 17/325,921, which was filed May 20, 2021 and entitled "Systems and Methods for Using Acoustic Communications for Contact Tracing within Administrative Boundaries," which also claims priority to U.S. Provisional Patent Application No. 63/032,587, which was filed May 30, 2020," all hereby incorporated by reference herein, each in its respective entirety.

FIELD

The present disclosure generally relates to the use of acoustic communication technology in computer systems. More particularly, the present disclosure relates to the use of acoustic communication technology in association with various types of computer systems and computing devices for the purpose of assessing epidemiologically significant exposure to various forms of disease.

BACKGROUND

Contact tracing generally refers to the process of identifying individuals who may have come into contact with a person infected by a communicable disease. By tracing the contacts of infected individuals, testing such contacts for infection, isolating and treating infected contacts, and tracing the contacts of exposed and infected individuals, organizations can reduce the spread of infectious disease. In particular, contact tracing becomes especially important during the rapid spread of disease associated with epidemics and pandemics. As such, a need exists for providing improved ways of performing contact tracing with greater efficiency, accuracy, and coverage.

SUMMARY

Aspects and advantages of embodiments of the present disclosure will be set forth in part in the following description, or can be learned from the description, or can be learned through practice of the embodiments.

One example aspect of the present disclosure is directed to a computer system that performs contact tracing using acoustic communications. For example, the computer system may include one or more processors and one or more non-transitory computer-readable media storing instructions that, when executed by the one or more processors, cause the computer system to perform operations. For example, such operations may include obtaining information associated with one or more acoustic tokens received from a first user device of a first user where the one or more acoustic tokens are associated with an emitter device that broadcasts acoustic tokens in an acoustic volume via an audio communication channel, obtaining information associated with one or more acoustic tokens received from a second user device of a second user where the one or more acoustic tokens are associated with the emitter device, determining whether the second user was exposed to a disease associated with the first user in the acoustic volume based on analyzing the information associated with the one or more acoustic tokens received from the first user device in view of the information associated with the one or more acoustic tokens received from the second user device, and outputting information based on the determining of whether the second user was exposed to the disease associated with the first user in the acoustic volume.

Another example aspect of the present disclosure is directed to a computer-implemented method for performing contact tracing based on acoustic communications. For example, a computer-implemented method performed by one or more processors may include obtaining information associated with one or more acoustic tokens received from a first user device of a first user where the one or more acoustic tokens are associated with an emitter device that broadcasts acoustic tokens in an acoustic volume via an audio communication channel, obtaining information associated with one or more acoustic tokens received from a second user device of a second user where the one or more acoustic tokens are associated with the emitter device, determining whether the second user was exposed to a disease associated with the first user in the acoustic volume based on analyzing the information associated with the one or more acoustic tokens received from the first user device in view of the information associated with the one or more acoustic tokens received from the second user device, and outputting information based on the determining of whether the second user was exposed to the disease associated with the first user.

A further example aspect of the present disclosure is directed to one or more tangible non-transitory computer-readable media storing computer-readable instructions that, when executed by one or more processors, cause the one or more processors of a computing device to perform operations. For example, the operations may include obtaining information associated with one or more acoustic tokens received from a first user device of a first user where the one or more acoustic tokens are associated with an emitter device that broadcasts acoustic tokens, obtaining information associated with one or more acoustic tokens received from a second user device of a second user where the one or more acoustic tokens are associated with the emitter device, determining whether the second user was exposed to a disease associated with the first user based on analyzing the information associated with the one or more acoustic tokens received from the first user device in view of the information associated with the one or more acoustic tokens received from the second user device, and outputting information based on the determining of whether the second user was exposed to the disease associated with the first user.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to those skilled in the art is set forth in the specification, which makes reference to the appended figures, in which.

DETAILED DESCRIPTION OF THE INVENTION

Figure 1:
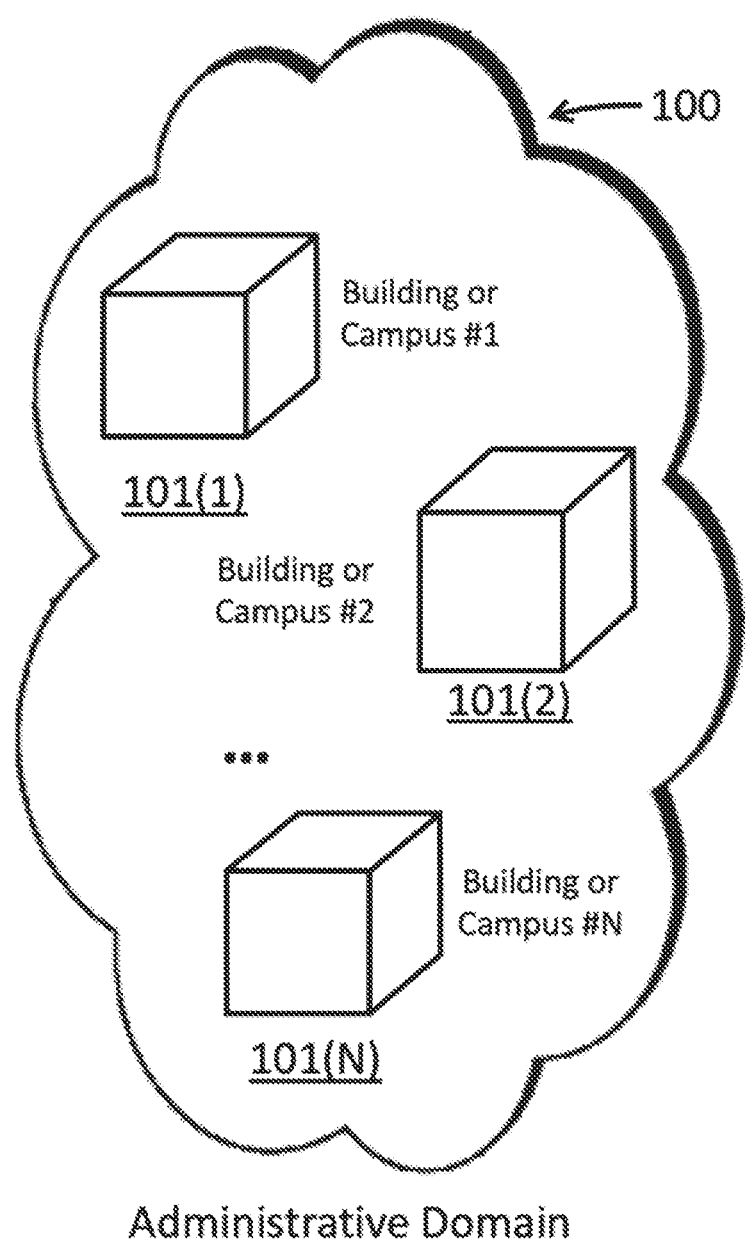
FIG. 1 is an illustration depicting an example of an administrative domain environment, according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a further embodiment. Thus, it is intended that aspects of the present disclosure cover such modifications and variations.

During periods of an endemic, epidemic, pandemic and/or any other spread of disease, there is a desire for employers (both public and private), service providers, and other entities to provide notice to employees, contractors, customers, and/or other parties that may have been exposed to a diseased person (e.g., a person infected with a communicable disease, a person believed to be infected with a communicable disease, etc.) for an epidemiologically significant amount of time. Embodiments in the present disclosure describe use of acoustic communications to provide such notification.

As an illustrative example, ultrasonic information may be transmitted from a variety of unified communications endpoints, such as videoconferencing systems, video phones, and the like, so that users may pair (e.g., associate) their endpoints (hereinafter "user endpoints") to those devices (hereinafter "system endpoints"). In an example, various types of systems may emit "information tokens" (e.g., acoustic tokens) from the system endpoints which, when received and decoded by user endpoints, are transmitted back to the videoconferencing system provider infrastructure in order to make an association between the system endpoint and the user's endpoint. For example, such various types of systems can be deployed in enterprise locations (e.g., businesses, governments, etc.) for use by employees.

In an example, such user endpoint devices (e.g., Mac® computers, PCs, and iOS® or Android® phones) may have software to decode the information tokens sent by the system endpoints where the user (e.g., an employee) has agreed to appropriate use of receiving and sending such token information in either their terms of employment (e.g., via an agreement) or by another appropriate opt-in, privacy policy, or terms-of-use provision.

In the normal operation of systems such as these, the information tokens (e.g., acoustic tokens) are frequently refreshed so that there is no long-term association between a specific token and a specific system endpoint. A valid token at one instant will become stale (e.g., have no useful value for pairing) a short time after such refresh, although a given token may be reused after an appropriate period of non-use. For this reason, these systems generally have little or no need to keep a long-term history of when a particular token was emitted from a given system endpoint in a given room at a given time.

Examples of the present disclosure change this paradigm to provide contact tracing within administrative boundaries, while still leveraging the concept of such tokens (e.g., acoustic tokens) being emitted from those system endpoints at a certain time and at a certain place. Examples of the present disclosure also describe an "information token allocation and delivery service," which provides unique tokens to system endpoints via standard networking services in association with other operations.

System endpoints such as these can be placed in specific acoustic volumes (e.g., a conference room, huddle room, private office, etc.) where sound-based communication techniques may be used, for example, instead of other potential pairing technologies (e.g., Bluetooth®). This is because sound-based communications can be made local to the desired acoustic volume. As such, it is important for the purposes of this disclosure to decouple physical-distance proximity from acoustic proximity. For example, two people on different sides of a common wall may be close to each other in a radio frequency (RF) sense but "not in proximity" to each other in an acoustic or epidemiologically significant sense. As such, two apartments with adjacent bedrooms can have cellphones that can communicate via Bluetooth® on end tables separated by as little as one meter from one another. However, the occupants of the different rooms pose little disease exposure risk due to the physical separation of the apartment-dividing wall. Similarly, this applies to office rooms in enterprise settings, many hospital room settings, and/or many other types of physical settings. Nonetheless, RF solutions (e.g., such as Bluetooth® beacons) may be used, for example, in conjunction or combination with examples of the present disclosure.

In the present disclosure, an "acoustic volume" is not limited to the typical sense of a space (e.g., the product of the length, width, and height of a rectangular room). Instead, an "acoustic volume" generally may refer to any space within which acoustic information transmission has been designed to take place or otherwise takes place from a specific system device to a user device that is nearby (e.g., to any user device that receives acoustic information transmitted by another device). Such user devices can be said to be in "acoustic proximity" to the system device. Also, there may be multiple "acoustic volumes" within a larger physical room's volume (or in any space), which may overlap with one another. In addition, "acoustic volumes" are not limited to enclosed, semi-enclosed, or indoor spaces and generally may include any type of open space, outdoor space, hybrid indoor-outdoor space, and/or any other type of space where transmission of acoustic information can occur from one device to another device. Related examples are provided in the embodiments described throughout the present disclosure.

One important objective of the present disclosure is to make an association between persons (or, more precisely, their user endpoints) that have been in epidemiologically significant proximity in a specific acoustic volume for an epidemiologically significant exposure time by use of the correlation of the identification tokens received by their user devices. For example, such correlation should normally occur after one (or more) of the persons is known to be diseased. This correlation may take place in a back-end or cloud setting where the relevant sent identification token information and received information token databases are used to make the correlation. In some examples, the entity making an association between specific user endpoints and specific system emitters is the local administrative domain or a larger federation of such administrative domains that already has obtained user consent to make such a correlation.

In the present disclosure, the definition of emitted identification tokens is expanded beyond information used to identify a system endpoint, such as a system endpoint mentioned in the unified communications example discussed above. For example, some optional information elements associated with the identification token may include, but are not limited to, one or more of time elements, duration elements, elements used to sound the impulse response of the room, acoustic ranging elements, and/or other elements that can be added for other system functions. Embodiments utilizing such information elements are further described below.

In the present disclosure, an element of an emitted identification token that can be used to identify an endpoint generally may be referred to as the "identification element," the "endpoint identification element," or the "emitter identification element" of the identification token. Such identification elements may be static identifier elements or ephemeral identifier elements (e.g., a dynamic identifier element, identifier elements that may change over time, etc.), and examples of both static and ephemeral identifier elements are described in embodiments below. Further, the terms "acoustic tokens," "identification tokens," "sent tokens," or "emitted tokens" generally refer to and may include an endpoint identification element plus any optional elements used in a particular system design.

The videoconferencing system example mentioned above is non-limiting and provided for illustrative purposes only. For example, the form of acoustic communication may be spread-spectrum or non-spread-spectrum based, may employ modulation of any form (e.g., AM, QAM, PSK, etc.) or be baseband, or occupy hearable and/or non-hearable (e.g., ultrasound) frequencies. Additionally, examples of the present disclosure may include the use of any other system and/or computing devices that are capable of both sound generation and network communication (e.g., IP phones). Many types of consumer devices include both audio output capabilities in excess of those required as well as the required networking capabilities (e.g., Raspberry Pi® with audio output, smart home computer devices, smart speaker devices and hardware, virtual assistant devices and hardware, wearable devices, etc.). These devices as well as other non-consumer devices (e.g., IoT devices, access-control hardware, smart building computing devices, industrial devices, and/or other machines with computing capabilities, etc.) or custom devices that can both emit acoustic tokens and communicate information to back-end infrastructure and databases can also be used as system devices.

Examples of the present disclosure may include the use of user devices other than the Mac® computers, PCs, and iOS® or Android® phones mentioned above as long as such devices have the required software, audio recording, and networking capabilities. Additionally, similar to the unified communications example, the users should have agreed to appropriate use of receiving such communications on their devices. Additionally, similar to the unified communications example above, the users should have agreed to appropriate use of receiving such communications on their devices.

Examples of the present disclosure may include the use of a specially designed system or any type of adjunct, improvement, and/or customization to an existing system (e.g., an access control system, a unified communications system, etc.) that can be made to operate in a similar manner (e.g., by emitting acoustic identification tokens from user endpoints to system endpoints, to user endpoints from system endpoints).

One important feature of example systems described in this disclosure is to enable an administrative domain to correlate an emitted identification token (or identification token sequence in some designs) sent sometime in the past to a specific system endpoint in association with performing contact tracing. Another important feature of example systems in the present disclosure is to determine from the emitted identification token or identification token sequence that a person (or more precisely, one or more user endpoints associated with the person) may have been within an epidemiologically significant proximity to a diseased person in a specific acoustic volume for an epidemiologically significant exposure time. For example, such a determination may be based on a correlation of the identification tokens received from respective user devices of the users with emitted identification tokens of system endpoints associated with the acoustic volume. As such, when a person provides notification to the administrative domain that they have tested positive for a disease of interest, then a correlation of their received identification tokens is made with received identification tokens of all other user endpoints in the administrative domain (or federation of administrative domains) to assess if the exposure criteria have been met. When such criteria have been met, then an appropriate notification is provided to other affected users.

In examples of the present disclosure, the sent endpoint identification elements and an appropriate set or subset of optional information elements useful for contact tracing purposes for all emitters should either be stored in a database or be generatable for a minimum of the worst-case time between exposure and symptomology, but for privacy reasons need not be stored for significantly longer.

In examples of the present disclosure, the received endpoint identification elements and an appropriate subset of optional information elements useful for contact tracing purposes for all receivers should be kept in a database for a minimum of the worst-case time between exposure and symptomology, but for privacy reasons need not be stored for significantly longer.

The database storing the received identification tokens of a given user endpoint may reside on the user endpoint itself or in external or cloud-based storage or both, depending upon a given embodiment. Owing to privacy and security purposes, the correlation process typically takes place on infrastructure under the control and management of the administrative domain and not on user devices.

Examples of the present disclosure may include system endpoint emitters that can operate without (e.g., do not require) network access and only require local power (e.g., battery power, solar power, alternating current power, etc.). Any such system endpoint emitter generally can be referred to as a "stand-alone emitter." As an example, the design characteristics of a stand-alone emitter may include: (1) not requiring network access to provide the emitter with an identification token from a token allocation operation after initial set-up or configuration, and (2) a design which accounts for events such as power outages that may cause synchronization issues between a specific stand-alone emitter and the token verification operation.

Examples of the present disclosure also may include the use of token/information exchange in the reverse direction (e.g., user device to system device) as well as bidirectional information exchanges between system endpoints and user endpoints. As one example, when the token/information exchange is performed in the reverse direction, the stand-alone emitter is the user device as the roles of the system endpoints and user endpoints (as described herein) are reversed. Accordingly, such embodiments are explicitly included in this disclosure.

Examples of the present disclosure also may include other mechanisms (e.g., Bluetooth®, iBeacon®, Wi-Fi, or GPS location triggers) that could initiate a system endpoint to user endpoint communication with acoustic communications and/or acoustic ranging techniques, for example, as described in this disclosure and following such initiation of communication. In examples of the present disclosure, use of the described acoustic techniques in conjunction with radio frequency (RF) contact tracing techniques can reduce false positives that may occur, for example, with RF-only techniques. Accordingly, such embodiments are explicitly included in this disclosure.

One important objective of the present disclosure is to provide a mechanism for employers (both public and private), service providers, and other entities to provide notice to their employees, contractors, customers, or others that may have been exposed to a diseased person for an epidemiologically significant duration or amount of time. For example, such notice can be associated with contact tracing and generally may be referred to as exposure notification. Examples of the present disclosure use acoustic communications techniques to enable such notification. Further, contact tracing and exposure notification generally may be referred to hereinafter as "CT".

Embodiments of the present disclosure use acoustic communications via system design enhancements and modifications of existing systems (which may or may not have CT as their primary function) or via new systems developed specifically for CT. An example of the former is the unified communications example described above. Examples of new systems designed for CT are provided in various example embodiments described herein.

While many systems can be enhanced and modified in view of examples in the present disclosure, the embodiments described herein generally focus on the key elements, configurations, operations, and other mechanisms to enable CT based on acoustic communications. For example, one or more such elements generally may include (1) one or more system endpoint devices that emit identification tokens acoustically (e.g., which may be referred to hereinafter as "system endpoints," "token emitters," or just "emitters"), (2) one or more user computing devices such as smartphones, laptops, wearable devices, and/or any other type of computing devices that may receive and decode the identification tokens sent acoustically (e.g., which may be referred to hereinafter as "user endpoints"), (3) an identification token allocation process ensuring that a given emitted identification token maps to a single specific system endpoint at any point in time for a given embodiment via system design or other infrastructure that allocates identification tokens, (4) one or more databases for storing and maintaining the received identification tokens, (5) and/or one or more databases for storing and maintaining the sent identification tokens.

The systems, methods, and computer program products described herein provide a number of technical effects and benefits. As one example, the embodiments described in the present disclosure provide various systems and methods for utilizing acoustic communications involving multiple computing devices to perform automated or semi-automated contact tracing more accurately and more efficiently within an administrative domain (or across a federation of administrative domains), than would otherwise be wasted by performing conventional or manual configuration and processing.

With reference to the Figures, example embodiments of the present disclosure will be discussed in further detail.

FIG. 1 depicts the concept of an Administrative Domain (AD) for the purposes of this disclosure. As an example, the AD 100 could be that of a private company that has employees, contractors, vendors, and the like that have the need to visit the buildings, offices or campuses of the company. Another example might be a hospital health system with various branches. In preferred embodiments, the CT described herein is local to an administrative domain (e.g., AD 100). As such, the appropriate user opt-in, privacy, and/or terms-of-use issues are local to the AD (a federation of ADs is discussed later). AD 100 includes individual buildings or campuses that are labeled as 101(1) through 101(N).

Figure 2:
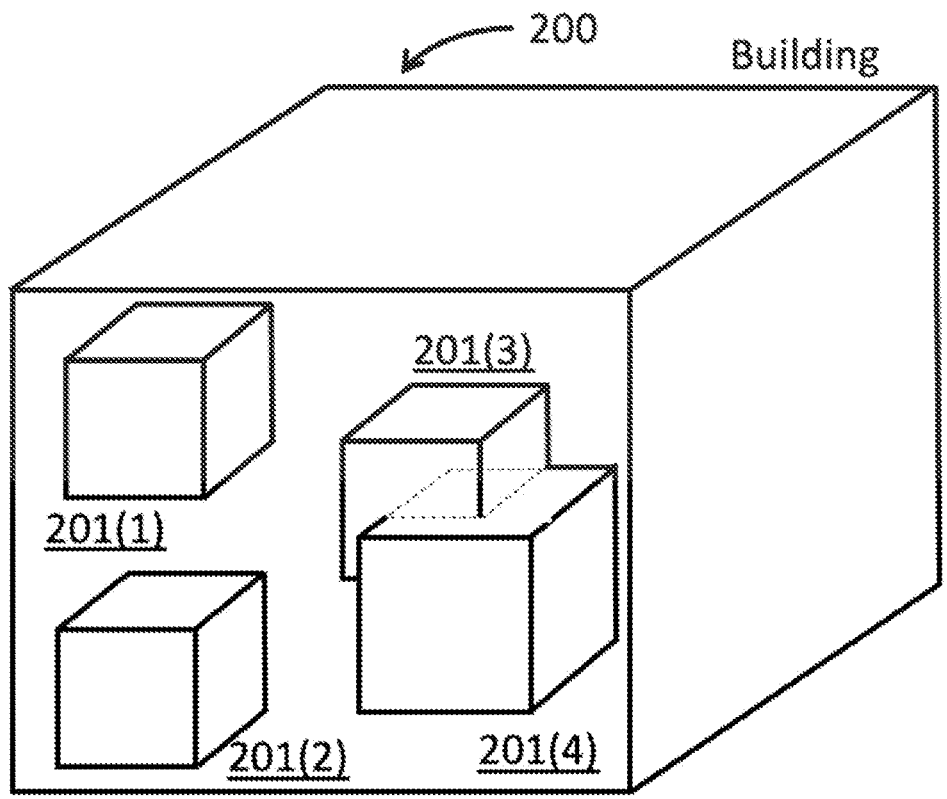
FIG. 2 is an illustration of an example of acoustic volumes, according to example embodiments of the present disclosure.

FIG. 2 is an illustration of an example of acoustic volumes, according to example embodiments of the present disclosure. In FIG. 2, a singular Building 200 includes one or more acoustic volumes ("AVs") labeled AV 201(1) through AV 201(4). As an example, one of these AVs might be a conference room or an individual's private office. These AVs are meant to show a space where acoustic communication of information tokens is local in the sense that user endpoints can decode the information tokens while within the AV. Also depicted are AVs where the volumes overlap, such as AV 201(3) and AV 201(4). This can occur because a user endpoint may be able to receive tokens being emitted from more than one AV. For example, multiple system endpoint emitters may also be placed in open floorplan arrangements in which the AVs may overlap. In particular, user endpoints in a given AV that belong to different users may be close enough and have exposure long enough for the purposes of CT described herein.

Figure 3:
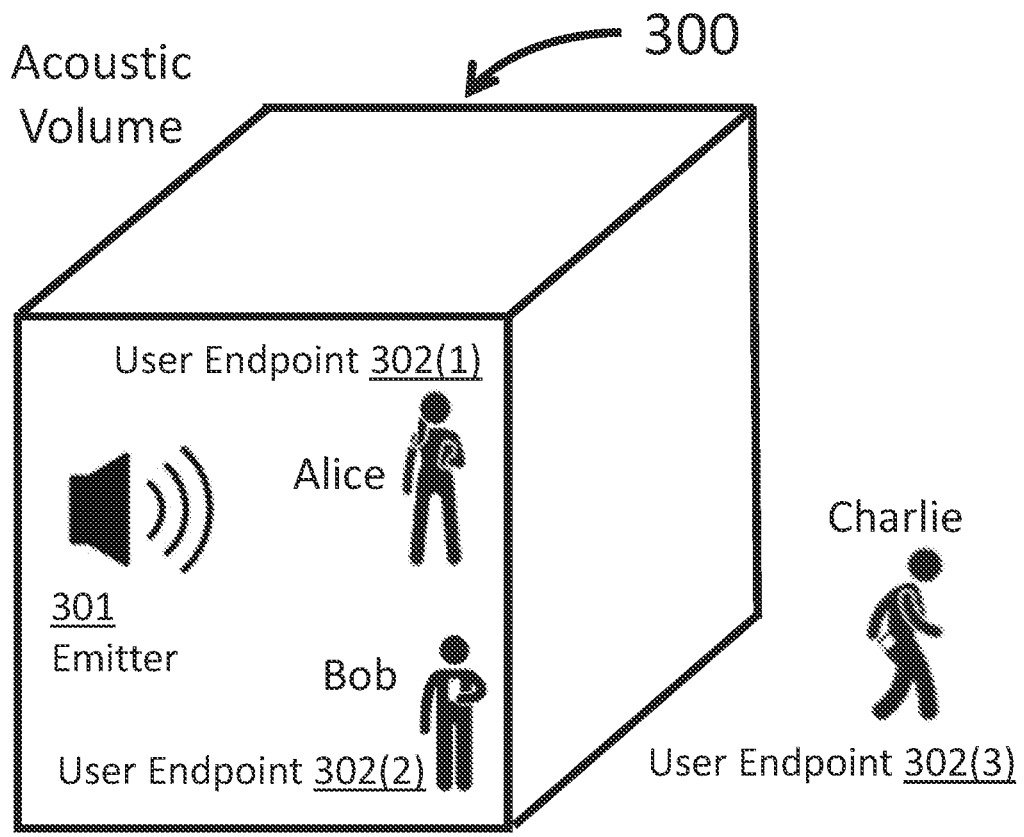
FIG. 3 is an illustration depicting an example environment with two users and an acoustic token-emitting system device within an acoustic volume and one user outside the acoustic volume, according to example embodiments of the present disclosure.

FIG. 3 depicts how users (more precisely their user devices) are associated with a given AV by means of decoding identification tokens local to an AV. FIG. 3 shows an example of an Acoustic Volume 300 where an information token Emitter 301 (e.g., a system endpoint) is emitting identification tokens. Two user endpoints (e.g., User Endpoint 302(1) and User Endpoint 302(2), belonging to Alice and Bob respectively) are in the same AV as information token Emitter 301, whereas User Endpoint 302(3) (belonging to Charlie) is not in Acoustic Volume 300. The system will make the association that Alice's and Bob's user endpoints are in Acoustic Volume 300 and will determine the time period of overlap where they (or their endpoints) both were in Acoustic Volume 300.

Example Embodiment One: Non-Privacy-Enabled Stand-Alone Emitter System Endpoint with Trusted User Endpoint In an embodiment, a system includes a stand-alone emitter (SAE) that periodically emits a static, unobfuscated emitter identification (ID) element, a trusted user endpoint, and a trusted user endpoint application. In the present disclosure the term "non-privacy-enabled" generally is used to indicate that no attempt is made to obfuscate the emitter ID element by changing the identification element of the emitter over time. Also, the term "trusted user endpoint" generally indicates that the user endpoint and an associated user application that processes received tokens (e.g., decodes and reports received tokens, provides received tokens to another device for decoding and reporting, etc.) are trusted by the AD. In some examples associated with the current embodiment, a mechanism to verify or bound the time accuracy of the timestamps for received tokens stored or reported by user endpoints may not be provided or utilized, for example, when all such endpoints are trusted.

Figure 4A:
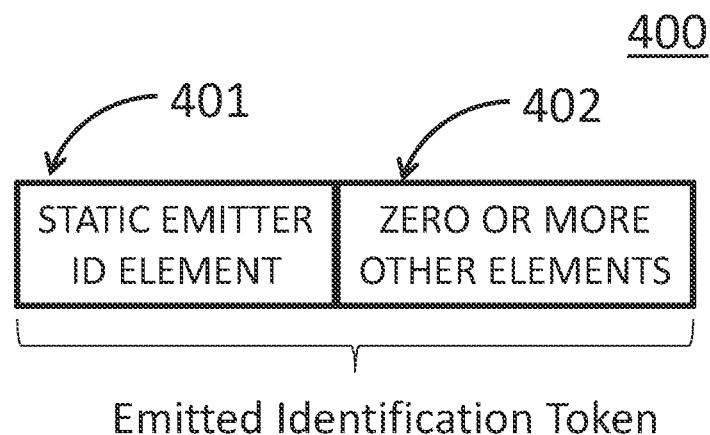
FIG. 4A is an illustration depicting an example payload format for an acoustically transmitted identification token, according to example embodiments of the present disclosure.
Figure 4B:
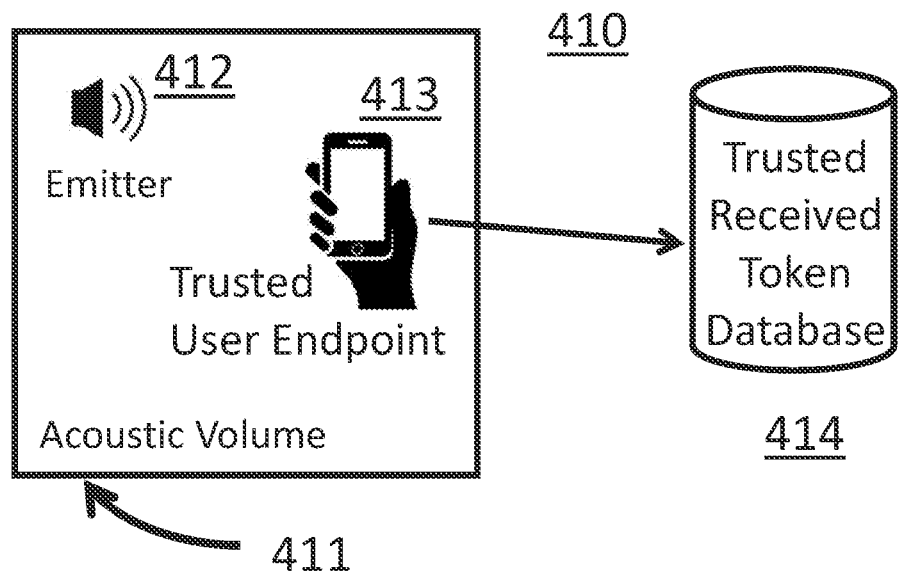
FIG. 4B is an illustration depicting an example of a trusted user endpoint in a specific acoustic volume communicating token information to a trusted received token database, according to example embodiments of the present disclosure.

FIG. 4A and FIG. 4B describe embodiments associated with providing a non-privacy-enabled stand-alone emitter with fully trusted user endpoints and user endpoint applications in which the stand-alone emitter periodically emits a static emitter identification element.

Other additional embodiments provided further below modify both these private/non-private and trusted/non-trusted assumptions to thwart the ability of potentially malicious, non-trusted user endpoints or non-trusted applications on otherwise trusted user endpoints, for example, to report acoustic events that did not occur, to modify events that did occur (e.g., such as timestamps) or to determine where a user went over the course of a given day (e.g., thus preserving privacy of user movement consistent with user consent).

FIG. 4A is an illustration depicting an example payload format for an acoustically transmitted identification token, according to example embodiments of the present disclosure. In an embodiment, FIG. 4A includes an example Payload Format 400 for acoustically transmitted identification tokens that are associated with an SAE (e.g., such as a non-privacy-enabled SAE system endpoint).

In an embodiment, the example Payload Format 400 comprises one or more fields, including a Static Emitter ID Element 401. Other information elements, referred to hereinafter as Other Elements 402, may be included with example Payload Format 400 data of an emitted identification token. In an example, Other Elements 402 may be optional, embodiment-specific elements that may, for example, include one or more of time elements, duration elements, elements used to sound the impulse response of the room, acoustic ranging elements and/or other elements that can be added for other system operations in different or enhanced embodiments.

In an embodiment, the size of the Static Emitter ID Element 401 can be configured to support a maximum number of system endpoints in the AD, and the Static Emitter ID Element 401 value is unique to a system endpoint (e.g., similar to a MAC address for ethernet addressing). In addition, the Emitter Identification Element Allocation Method provides a 1:1 mapping of any system endpoint to its respective Static Emitter ID Element 401 value.

FIG. 4B is an illustration depicting an example of a trusted user endpoint in a specific acoustic volume communicating token information to a trusted received token database, according to example embodiments of the present disclosure. In an embodiment, FIG. 4B includes System 410 where an Emitter 412 (e.g., such as a non-privacy-enabled SAE system endpoint) and a Trusted User Endpoint 413 are in a specific Acoustic Volume 411. Emitter 412 periodically transmits an emitted identification token (e.g., based on the example Payload Format 400) and the Trusted User Endpoint 413 receives the token. The periodicity with which Emitter 412 emits tokens can be determined based on the minimum time resolution for exposure event reporting and, thus, may be chosen consistent with the minimum exposure time of an exposure event for a communicable disease.

In an embodiment, an application from a Trusted User Endpoint 413 decodes an identification token and creates a database record comprising the Static Emitter ID Element 401, any Other Element(s) 402 associated with the identification token (e.g., as implemented in a particular embodiment), and a timestamp of when the information token was received. The application of the Trusted User Endpoint 413 then saves the database record to the Trusted Received Token Database 414. In some embodiments, the application of the Trusted User Endpoint 413 may provide an identification token and/or information associated with the identification token to another computing system or computing device (e.g., one or more server machines) that may perform one or more operations associated with processing an identification token (e.g., such as decoding the identification token) and storing associated information in the Trusted Received Token Database 414.

Although shown as a single Trusted Token Received Token Database 414, those skilled in the art will recognize that in some examples data may be stored entirely on the Trusted User Endpoint 413 or conveyed via a network and stored sometime afterwards in some other infrastructure (e.g., such as a cloud storage infrastructure). Those skilled in the art also will recognize that if data synchronization techniques are employed between the Trusted User Endpoint 413 and the Trusted Received Token Database 414, some database records may only exist on the Trusted User Endpoint 413 until synchronization of such database records with the Trusted Received Token Database 414 is complete. In various embodiments, the individual token reception events are stored as database records (e.g., as trusted database records) in the Trusted Received Token Database 414. In various embodiments, the Trusted Received Token Database 414 is intrinsically trusted (not needing verification via other substantiating information or processing) by some or all of the user endpoints. Additionally, as the Trusted Received Token Database 414 includes CT-related data and other private data, this database should be protected appropriately and only accessed by authorized AD personnel, applications, and processes.

Figure 5:
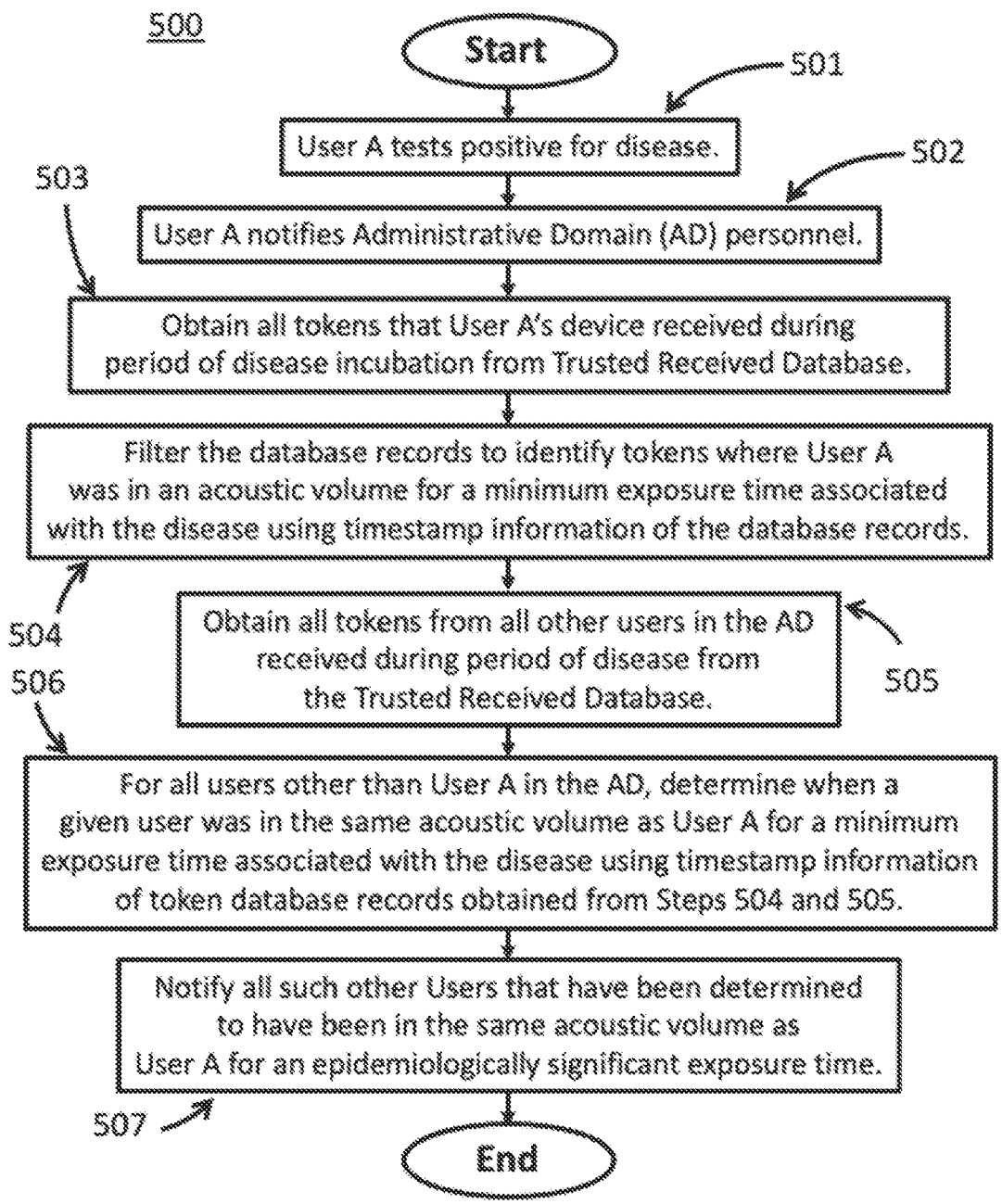
FIG. 5 is a flow diagram of an example method for performing contact tracing and notification, according to example embodiments of the present disclosure.

FIG. 5 is a flow diagram of an example method 500 for performing contact tracing and notification, according to example embodiments of the present disclosure. One or more portions of the example method 500 can be executed and/or implemented on one or more computing devices or computing systems. In addition, one or more portions of the example method 500 can be executed or implemented as an algorithm on the hardware devices or systems disclosed herein. FIG. 5 depicts steps performed in a particular order for purposes of illustration and discussion. As such, those skilled in the art, using the disclosures provided herein, will understand that various steps of any of the methods described herein can be adapted, modified, rearranged, omitted, and/or expanded without deviating from the scope of the present disclosure.

At Step 501, a user within the scope of an AD of this disclosure (e.g., "User A"), learns that they have tested positive for a disease. At Step 502, "User A" notifies the AD personnel or the contact tracing system of their positive test result, for example, by calling, by messaging, by email, or via direct interaction with a contact tracing application user interface provided via a computing device (e.g., provided via a user device of "User A").

At Step 503, "User A's" token information (e.g., trusted database records) received, for example, during one or more of an incubation period, an infection period, and/or a contagious period of the disease associated with "User A" are obtained from the Trusted Received Token Database 414. For example, "User A's" token information may be determined or otherwise identified based on comparing one or more time periods associated with the disease to trusted database timestamps of trusted database records associated with "User A".

At Step 504, the subset of trusted database records obtained at Step 503 is filtered to provide a further subset of database records, which meet the AV and minimum exposure time criterion appropriate for the disease (e.g., also using trusted database timestamp information associated with the trusted database records). For example, a set of trusted database records obtained at Step 503 may be searched, filtered, and/or otherwise processed to identify information tokens where "User A" (e.g., based on information associated with one or more devices of "User A") was in an acoustic volume for a minimum exposure time associated with a disease based on trusted database timestamp information of the trusted database records associated with "User A".

At Step 505, one or more trusted database records from each of one or more other user endpoints in the AD (e.g., all trusted database records associated with all user endpoints other than any user endpoint of "User A") received during one or more of the disease incubation period, the disease infection period, and/or the disease contagious period are obtained from the Trusted Received Token Database 414. In an example, Step 505 may be analogous to Step 503 for user endpoints other than "User A's" endpoint(s). For example, token information (e.g., trusted database records) received from other user endpoints, for example, during one or more of an incubation period, an infection period, and/or a contagious period of the disease associated with "User A" can be obtained from the Trusted Received Token Database 414. Such token information of other users may be determined or otherwise identified based on comparing one or more time periods associated with the disease to trusted database timestamps of trusted database records associated with the other users.

At Step 506, the token/record information obtained at Step 504 (e.g., relevant tokens of "User A") and at Step 505 (e.g., relevant tokens for users other than "User A") are analyzed based on timestamp information associated with the respective database records to determine whether a given user was in the same AV as "User A" for the minimum exposure time associated with the disease. At Step 507, users that have been exposed or that may have been exposed to "User A" for an epidemiologically significant exposure time are notified. For example, all users across one or more ADs that have been determined to have been in the same AV as "User A" for an epidemiologically significant exposure time (e.g., as determined at Step 506) are notified. For example, each of the other users determined to have been exposed or that may have been exposed to the disease may be notified via a CT tracing application on a user device, such as a user endpoint or any other device.

Persons skilled in the art will appreciate that some of the aforementioned steps can occur in parallel and/or in a different order to achieve the same result. Persons skilled in the art will also appreciate that the form of notification may provide information beyond a simple notification that one such contact has occurred, such as duration of the contact, the number of times such contact occurred, etc., for example, consistent with one or more AD policies on such matters. Further, in various embodiments, any one or more of the steps of method 500 or all of the steps of method 500 may be performed as a computerized process executed by one or more computing devices (e.g., software code executed by one or more processing devices), which perform such operations automatically, or on behalf of or upon request by appropriate AD personnel.

Example Embodiment Two: Non-Privacy-Enabled Stand-Alone Emitter System Endpoint with a Combination of Trusted User Endpoints and Non-Trusted User Endpoints In an embodiment, an SAE periodically emits a static, unobfuscated emitter ID element with a pseudo-random time element in an environment that comprises a combination of one or more trusted user endpoints and one or more non-trusted user endpoints. A "non-trusted user endpoint" generally refers to a user endpoint that includes one or more of user endpoint hardware and/or a user endpoint application (e.g., any contact tracing application or any other type of application such as a social media or videoconferencing application that provides contact tracing as a feature or add-on), which are not trusted by the AD. In some examples (e.g., similar to Example Embodiment One above), no attempt is made in this embodiment to obfuscate the emitter ID element by changing the emitter ID element over time. However, in some examples, this embodiment may include one or more operations for verifying the timestamps of the received tokens stored by the non-trusted endpoints. For example, such verification may be performed to prevent replay attacks that attempt to reuse a series of one or more tokens that have already been played out.

Figure 6A:
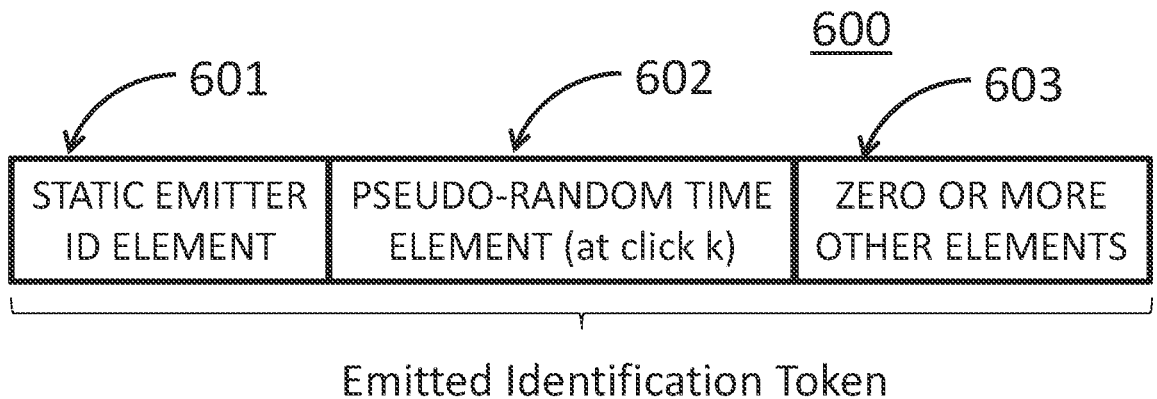
FIG. 6A is an illustration depicting an example payload format for an acoustically transmitted identification token, according to example embodiments of the present disclosure.

FIG. 6A is an illustration depicting an example payload format for an acoustically transmitted identification token, according to example embodiments of the present disclosure. FIG. 6A includes an example Payload Format 600 for acoustically transmitted identification tokens associated with an SAE (e.g., such as a non-privacy-enabled SAE system endpoint). In an embodiment, example Payload Format 600 includes at least two fields, a Static Emitter ID Element 601 and a Pseudo-Random Time Element 602. Other information elements, referred to hereinafter as Other Elements 603, may be included with example Payload Format 600 data of an emitted identification token. In an example, Other Elements 603 may be optional, embodiment-specific elements that may, for example, include one or more of time elements, duration elements, elements used to sound the impulse response of the room, acoustic ranging elements and/or other elements that can be added for other system operations in different or enhanced embodiments.

In an embodiment, the size of the Static Emitter ID Element 601 can be configured to support a maximum number of system endpoints in the AD, and the Static Emitter ID Element 601 value is unique to a system endpoint. In addition, the Emitter Identification Element Allocation Method for this embodiment provides a 1:1 mapping of any system endpoint to its respective Static Emitter ID Element 401 value.

In an embodiment, the Pseudo-Random Time Element 602 is a time-varying component used to verify the individual token reception records from Non-trusted User Endpoints so that records of such endpoints can be trusted by the AD. For example, such verification may be performed to detect and prevent replay attacks based on information of tokens that have already been played out. Examples describing the manner in which the Pseudo-Random Time Element 602 changes will be discussed in FIG. 7.

In some examples, the Static Emitter ID Element 601 may be sent in the clear. In such examples, a malicious endpoint (or endpoints) or some process knowing all the static emitter IDs in the AD and the emitter records of a given user endpoint (e.g., "User Z") possibly could determine the daily routine of "User Z", resulting in a lack of privacy. Further below, example Embodiment Three further discusses embodiments for providing enhanced privacy.

Figure 6B:
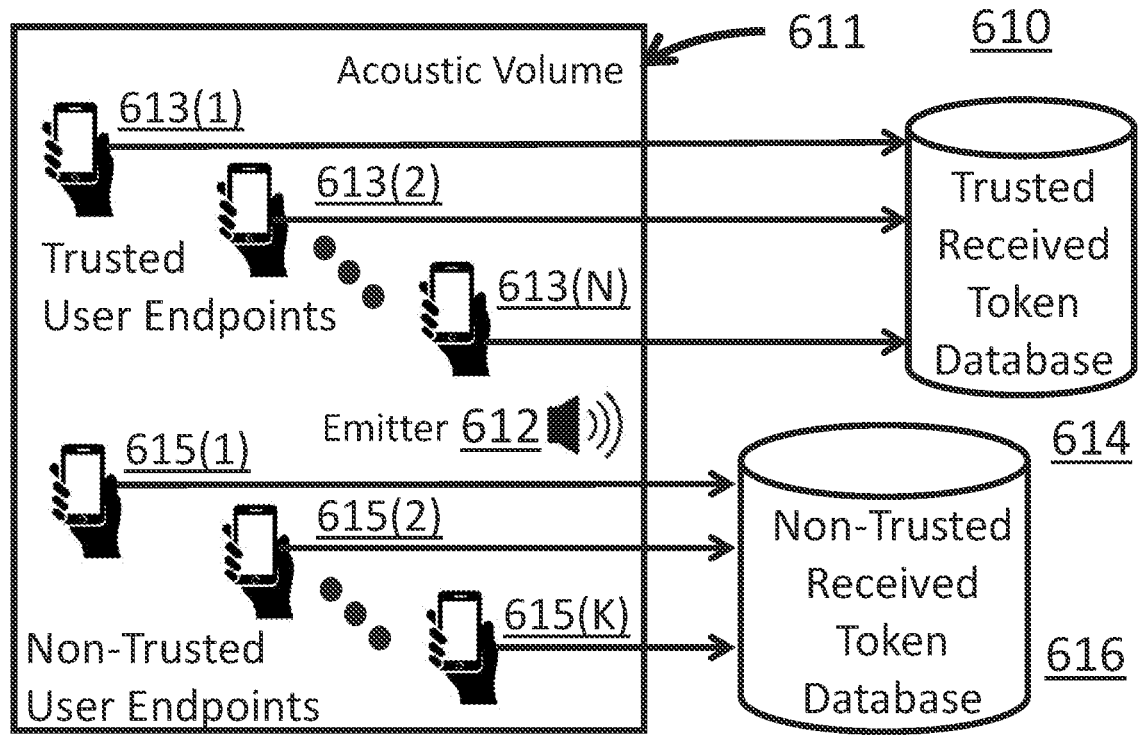
FIG. 6B is an illustration depicting an example of trusted user endpoints in an acoustic volume communicating token information to a trusted received token database and non-trusted user endpoints in the acoustic volume communicating token information to a non-trusted received token database, according to example embodiments of the present disclosure.

In an embodiment, FIG. 6B is an illustration depicting an example of trusted user endpoints in an acoustic volume communicating token information to a trusted received token database and non-trusted user endpoints in the acoustic volume communicating token information to a non-trusted received token database, according to example embodiments of the present disclosure.

In an embodiment, FIG. 6B includes a System 610 with an Emitter 612 (e.g., an SAE), one or more trusted user endpoints labeled Trusted User Endpoint 613(1) through Trusted User Endpoint 613(N), and one or more non-trusted user endpoints labeled Non-Trusted User Endpoint 615(1) through Non-Trusted User Endpoint 615(K), in an Acoustic Volume 611. In some examples, System 610 may include zero or more Trusted User Endpoints 613 and/or zero or more Non-Trusted User Endpoints 615.

In an embodiment, Emitter 612 periodically emits tokens to both trusted endpoints and non-trusted endpoints (e.g., similar to Emitter 412 of System 410). In addition, each of one or more Trusted User Endpoints 613(1)-613(N) sends one or more records (e.g., that each comprise received Payload Format 600 record information along with timestamps of when such records were received by respective trusted user endpoints) to the Trusted Received Token Database 614 (e.g., similar to processing performed by Trusted User Endpoint 413 of System 410). Further, each of one or more Non-Trusted User Endpoints 615(1)-615(N) sends one or more records (e.g., that each comprise received Payload Format 600 record information along with timestamps of when such records were received by respective non-trusted endpoints) to the Non-Trusted Received Token Database 616.

In an embodiment, the individual records in the Non-Trusted Received Token Database 616 undergo a verification process. An example of such verification is described in further detail below based on FIG. 7B. The records that have been verified can be moved (e.g., removed from the Non-Trusted Received Token Database 616), copied, or otherwise provided to the Trusted Received Token Database 614, and unverifiable records may be deleted from the Non-Trusted Received Token Database 616.

In an embodiment, the verification process for non-trusted user endpoint records uses the received Pseudo-Random Time Element 602 of example Payload Format 600 via an example process described in further detail below. As both the Trusted Received Token Database 614 and the Non-Trusted Received Token Database 616 contain CT-related data and other private data, these databases should be protected appropriately and only accessed by authorized AD personnel, applications, and processes. Further, the Trusted Received Token Database 614 and the Non-Trusted Received Token Database 616 are shown as separate databases in System 610 for purposes of explanation. However, those skilled in the art can appreciate that such databases may be implemented as one received token database, for example, with elements within the database records indicating whether the record is trusted or non-trusted.

In an embodiment, a system generates a pseudo-random time element (e.g., such as Pseudo-Random Time Element 602) for each of one or more respective system endpoints, which then may be used for verifying individual non-trusted user endpoint records of a non-trusted received database (e.g., such as records in Non-Trusted Received Token Database 616).

Figure 7A:
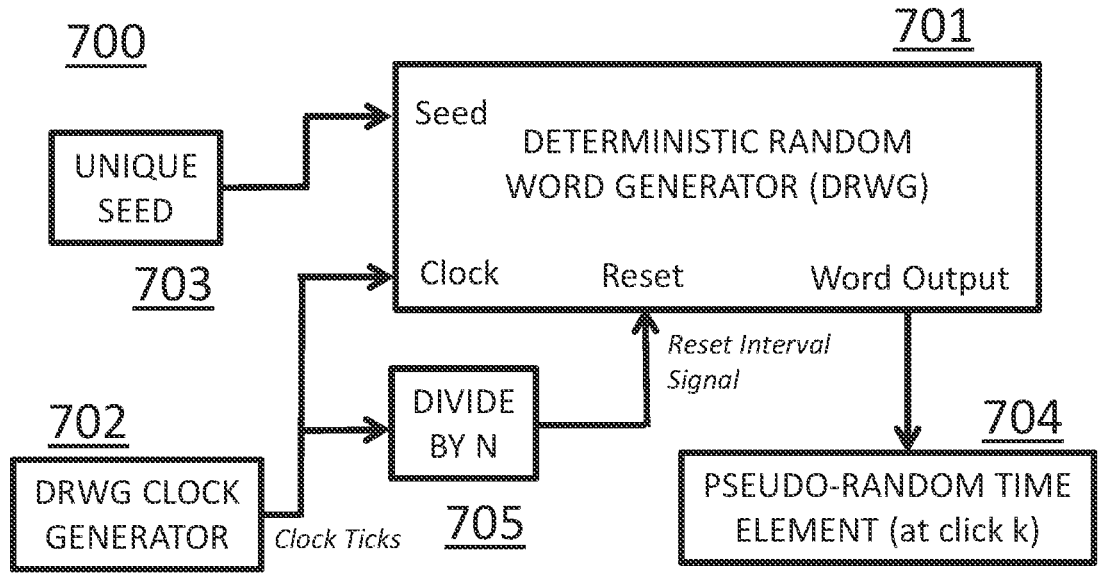
FIG. 7A is an illustration depicting an example embodiment for generating a pseudo-random time element for an emitter device, according to example embodiments of the present disclosure.

FIG. 7A is an illustration depicting an example embodiment for generating a pseudo-random time element for an emitter device, according to example embodiments of the present disclosure. FIG. 7A includes an example System 700 for generating a pseudo-random time element (e.g., Pseudo-Random Time Element 602) for a specific system endpoint emitter (e.g., Emitter 612). In an embodiment, the value of the Pseudo-Random Time Element 602 periodically changes over time, with the goal of ensuring that the series of such values cannot be predicted by a given user endpoint (or any other party or device). For example, such unpredictability can prevent a malicious user endpoint from replaying an existing token report at some future time. In particular, this design provides randomly appearing values (from the perspective of a user endpoint) that are in fact deterministic for the entity that generates the values. System 700 includes a deterministic random word generator, DRWG 701, for generating such values. In various examples, DRWG 701 generally may include or refer to deterministic random bit generators, pseudo-random noise sources, maximum-length binary sequence generators, pseudorandom number generators, or pseudo-random bit generators. For example, such devices generally may be used in communications, cryptography, and/or various other types of systems. In various examples, deterministic random word generator (e.g., DRWG 701) devices include a clocking mechanism and an initial value commonly known as a "seed."

System 700 includes Unique Seed 703 as the seed for a specific system endpoint emitter. In an embodiment, Unique Seed 703 can be used to determine both an initial word output and a deterministic series of word outputs. Effective DRWGs (e.g., such as DRWG 701) can produce very different outputs that appear random, even from slightly different seeds. In an embodiment, a seed is associated with a specific emitter (i.e., specific to the Static Emitter ID Element 601). In contrast, other designs derive the seed value from the Static Emitter ID Element 601 (e.g., via a one-way hash function). Clock transitions (hereinafter also referred to as clock "ticks") are produced by the DRWG Clock Generator 702 and define when a new Pseudo-Random Time Element 602 will be generated for the respective emitter. The period of time between clock transitions (e.g., the time between ticks) defines the time resolution of the verification process, which will be described in further detail below. The inter-tick period should be chosen such that replay attacks of malicious user endpoints are sufficiently thwarted.

System 700 includes Pseudo-Random Time Element 704, which generally represents a new Pseudo-Random Time Element 602. In some examples, changing the Pseudo-Random Time Element 704 once every three minutes may be enough for a minimum disease exposure time of 10 minutes or so (~500 ticks per day). Note that the exposure-time resolution estimate for the entire system (e.g., an acoustic contact tracing system) is dependent on the time resolution of the individual database records (i.e., user endpoint timestamps of records) and on the system endpoint emission intervals, but not directly on the DRWG inter-tick interval.

Figure 7B:
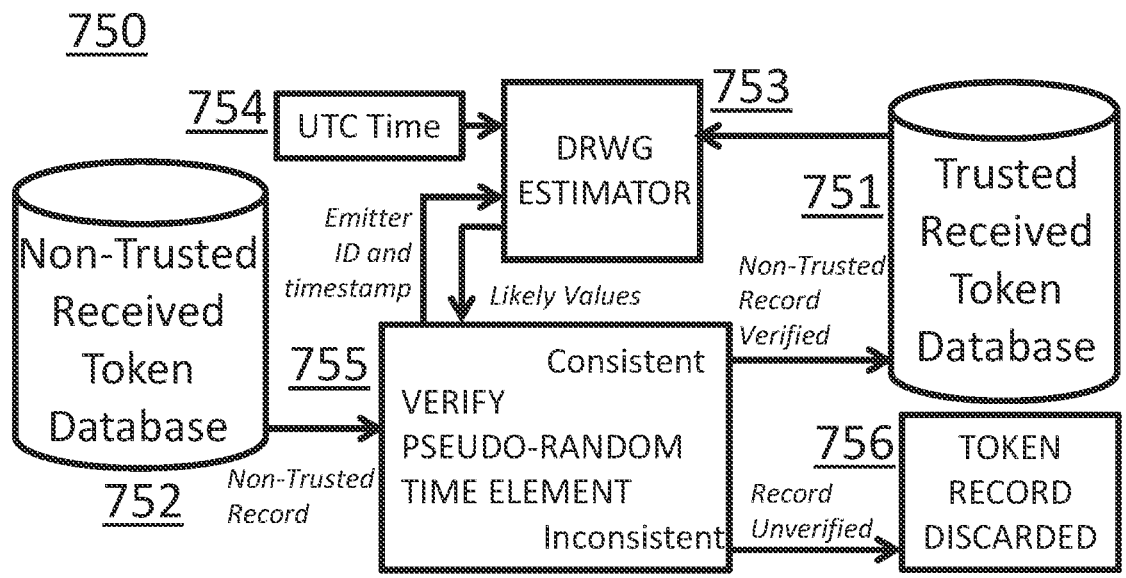
FIG. 7B is an illustration depicting an example embodiment for verifying individual token records of a non-trusted received database, according to example embodiments of the present disclosure.

In the verification process of FIG. 7B, it may be beneficial to limit the scope of values that a given emitter can produce, which can be achieved via the Divide by N 705 of System 700. In an embodiment, after N clock ticks the DRWG 701 resets and then repeats the same N values as initially produced. The value of N generally should be chosen to minimize malicious endpoints ever recalling—for malicious replay purposes—the sequence of N values. It is desirable to save the state of DRWG 701 and Divide by N 705 after every click (i.e., after the change of Pseudo-Random Time Element 704) in non-volatile memory so that the sequence order survives any power outage affecting example System 700. For example, a power loss in excess of the tick interval will cause discontinuity in the relationship between real time (e.g., Coordinated Universal Time, or UTC) and the DRWG Clock Generator 702 time (the click number), but one in which the DRWG Clock Generator 702 time is guaranteed to be monotonically increasing (thus, the Pseudo-Random Time Element 704 will continue the designed series of values). Persons skilled in the art will realize that the embodiments describe only some of many possible ways to meet the goals of a deterministically generated sequence of randomly appearing words for generating a Pseudo-Random Time Element 704.

FIG. 7B is an illustration depicting an example embodiment for verifying individual token records of a non-trusted received database, according to example embodiments of the present disclosure. FIG. 7B includes an example Token Verification System 750 for verifying emitter token records from non-trusted user endpoints. In an embodiment, the Non-Trusted Received Token Database 752 may be identical or otherwise corresponds to the Non-Trusted Received Token Database 616, and the Trusted Received Token Database 751 may be identical or otherwise corresponds to the Trusted Received Token Database 614.

In an embodiment, a verification process associated with Token Verification System 750 periodically occurs where individual records in the Non-Trusted Received Token Database 752 are analyzed (e.g., tested) to see whether the pseudo-random time element (e.g., Pseudo-Random Time Element 602) of that non-trusted record is within a range of expected values. As such, that verification process may determine that an existing non-trusted record now can be trusted, provide the associated record to the Trusted Received Token Database 751 (e.g., move, copy, etc.), and remove the associated record from the Non-Trusted Received Token Database 752.

In an embodiment, each of one or more records (e.g., every record) in the Non-Trusted Received Token Database 752, the Static Emitter ID Element 601 for each respective record, and the received timestamp for the respective record are provided to a DRWG Estimator 753. The DRWG Estimator 753 estimates the likely values of the DRWG output progression (that is, the series of Pseudo-Random Time Element 704 values) at a specific UTC time for every system endpoint emitter. The DRWG Estimator 753 operation consults the Trusted Received Token Database 751 for records containing the Static Emitter ID Element 601 that have received timestamps closest to the record in question. From those records, the DRWG Estimator 753 produces one or more likely values for the Pseudo-Random Time Element 602 of the non-trusted record. The Verify Pseudo-Random Time Element 755 operation compares the likely Pseudo-Random Time Element 602 values provided by the DRWG Estimator 753 to the actual value in the non-trusted record. If a match to one of the likely values is obtained, the record is verified and this record is moved to the Trusted Received Token Database 751, whereupon the verified record can be used to help verify future unverified records. If a match to one of the likely values is not found, then this record is discarded (i.e., deleted from the Non-Trusted Received Token Database 752) via the Token Record Discard 756 operation. Persons skilled in the art will recognize embodiments associated with the example Token Verification System 750 may be implemented in a variety of other ways to obtain the same result or similar results. In some embodiments, the DRWG Estimator 753 may use an indication of the present time by having the current universal time provided to it via the UTC Time 754 operation shown. In an example, the input of the current time may enable the DRWG Estimator 753 to predict the Pseudo-Random Time Element 602 at a recent time instant for exception cases, such as when a given emitter may have had a power outage (e.g., or with any other event causing a discontinuity between the current time and the DRWG Clock Generator 702 time, as noted earlier).

In some embodiments, one or more of the non-trusted records that do not pass verification (e.g., after the first attempt at verification or some other number of verification attempts) may continue to remain in the Non-Trusted Received Token Database 752. For example, the verification process may be repeated one or more additional times, and the non-trusted records then may be discarded after some number of unsuccessful verification attempts (e.g., a counter element may be used to track a number of unsuccessful verifications for each non-trusted record). Such operation(s) may have utility, for example, when only non-trusted user endpoints have been in the AV of interest in a recent period of time and where a crowdsourced method of estimating the likely Pseudo-Random Time Element 602 values from some number of non-trusted records is employed. In some embodiments verification of non-trusted records in the Non-Trusted Received Token Database 752 may be deferred, for example, if tokens are close to the current UTC time, as this may provide the DRWG Estimator 753 an ability to predict likely values with increased confidence (e.g., as the DRWG Estimator 753 can use data after the non-trusted record timestamp for the predicting the likely values).

In an embodiment, at some future time when a given user (e.g., "User A") tests positive for a disease, the process of notification may be similar or identical to example method 500 for performing contact tracing and notification. For example, trusted database records may be used in association with the notification process while non-trusted records can be excluded from such processing.

Example Embodiment Three: Privacy-Enabled Stand-Alone Emitter System Endpoint

In an embodiment, a privacy-enabled, stand-alone emitter periodically emits an ephemeral emitter identification element to one or more of trusted user endpoints and/or non-trusted user endpoints. Such identification elements can be received and processed by each of one or more user endpoint applications (e.g., one or more client applications, one or more server applications, one or more cloud applications, etc.) associated with respective user endpoints.

In an embodiment, an emitter ID element for an SAE is an ephemeral identifier that changes over time. As such, any party observing emitter ID elements received by a specific user endpoint would not know a reason for a change (e.g., whether the user endpoint changed location to a new AV or the user remained in the same AV and the change occurred based on another reason). Thus, a party observing the emitter ID elements (e.g., in one or more database records) cannot correlate the specific emitter ID element value to a specific AV or a specific system endpoint emitter associated with the AV.

In various embodiments, the inability of an observer to correlate a specific ephemeral emitter ID element value to a specific system endpoint emitter adds a significant measure of privacy to a CT system. For example, an adversary could only trace specific user endpoint movements through multiple AVs if it: (1) knew precisely how the ephemeral ID element changed in every AV where the specific user endpoint traveled, or (2) had multiple user endpoint accomplices observing the same tokens in all the multiple AVs where the specific user endpoint traversed (and such accomplice user endpoints reported the collected information back to the adversary). If we assume the latter is not likely or feasible within an AD, a significant measure of privacy can be attained by making the process of generating the ephemeral emitter ID element value as unpredictable as possible.

In some embodiments, CT systems of the present disclosure may include a maximum number of system endpoints in the range of 100,000 for an AD, which is of much smaller scale relative to a large-scale beacon strategy (e.g., beacon strategies involving hundreds of millions of endpoints). This smaller scale allows for a tradeoff in the complexity required for both assigning and resolving the ephemeral IDs to/from the system endpoint emitters.

The examples discussed are only some of many possible ways to provide similar or the same operations for CT based on acoustic communications. Further, Example Embodiment Three is unlike the prior two example embodiments (i.e., Example Embodiment One and Example Embodiment Two) in that the Emitter Identification Element Allocation Method is one in which the Ephemeral Emitter ID Element 801 changes over time, but at a given point in time is unique to a specific system endpoint as described below.

Figure 8A:
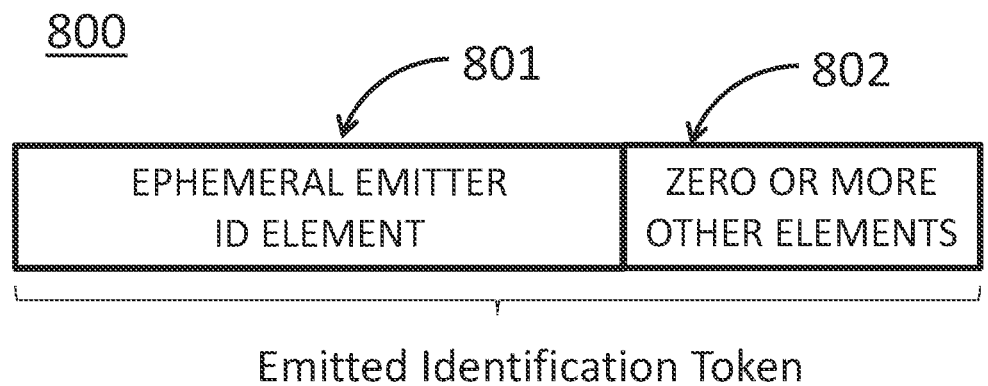
FIG. 8A is an illustration depicting an example payload format for an acoustically transmitted identification token, according to example embodiments of the present disclosure.

FIG. 8A is an illustration depicting an example payload format for an acoustically transmitted identification token, according to example embodiments of the present disclosure. FIG. 8A includes an example Payload Format 800 for acoustically transmitted identification tokens associated with an SAE (e.g., such as a non-privacy-enabled SAE system endpoint). In an embodiment, example Payload Format 800 includes at least one field, an Ephemeral Emitter ID Element 801. Other information elements, referred to hereinafter as Other Elements 802, may be included with example Payload Format 800 data of an emitted identification token. In an example, Other Elements 802 are optional, embodiment-specific elements that include one or more of time elements, duration elements, elements used to sound the impulse response of the room, acoustic ranging elements and/or other elements that can be added for other system operations in different or enhanced embodiments. In an embodiment, the Ephemeral Emitter ID Element 801 (referenced hereinafter as "ephemeral ID") may be larger than the static emitter ID elements of Example Embodiment One and Example Embodiment Two, for example, to provide additional privacy and to simplify the configuration and system operations as described below.

Figure 8B:
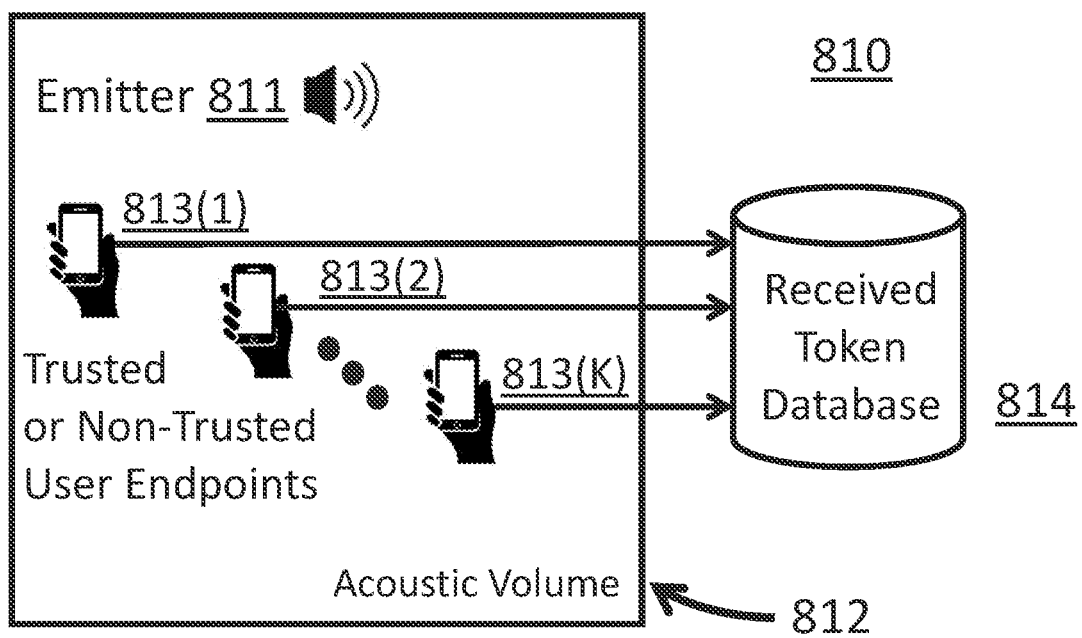
FIG. 8B is an illustration depicting trusted or non-trusted user endpoints in a specific acoustic volume communicating token information to a received token database, according to example embodiments of the present disclosure.

FIG. 8B is an illustration depicting trusted or non-trusted user endpoints in a specific acoustic volume communicating token information to a received token database, according to example embodiments of the present disclosure. FIG. 8B includes a System 810 that comprises an SAE labeled Emitter 811 and multiple, trusted or non-trusted user endpoints labeled 813(1) through 813(K) in an Acoustic Volume 812.

In an embodiment, differentiation between records of trusted user endpoints and records of non-trusted user endpoints may not exist, as records from all endpoints can go through the same verification process for processing of respective ephemeral IDs. For example, the user endpoints can send received tokens (e.g., as database records) to the Received Token Database 814, and the CT-related processing can take place outside of the user endpoints for privacy and security reasons. In some examples, the synchronization process of transferring individual database records associated with the received tokens to the Received Token Database 814 may not necessarily occur in real time. Instead, such transfer may occur at some future time, for example, when network connectivity is present, may occur in batches (e.g., as synchronization procedures allow), etc.

In an embodiment, a respective set of one or more ephemeral emitter identification element values is allocated to each of one or more corresponding system endpoints for the play out of the set of such ephemeral emitter identification element values from its corresponding individual system endpoint (e.g., based on the stand-alone emitter embodiment of FIG. 8). For example, a specific set of ephemeral IDs may be assigned to each specific system endpoint where such ephemeral IDs are reported from the specific user endpoints and are used to map the specific user endpoints to the specific system endpoint emitters and corresponding AVs.

Figure 9A:
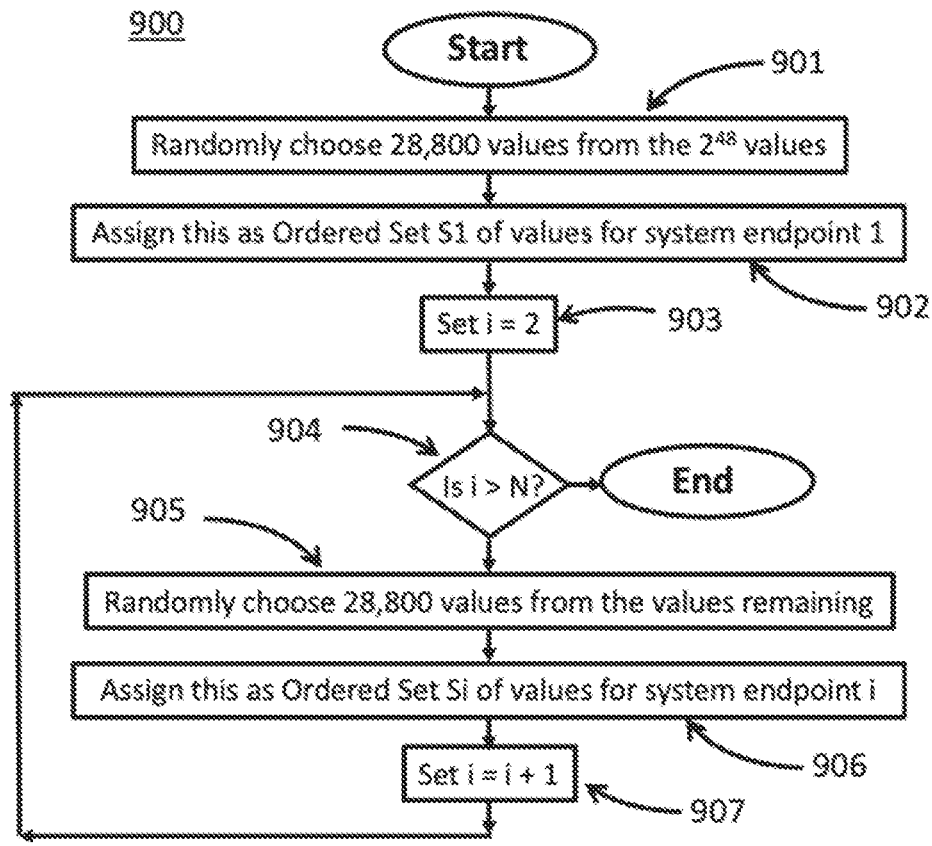
FIG. 9A is a flow diagram of an example method for the creation of ordered sets of ephemeral emitter identification element values and a mapping of those ordered sets to specific system endpoints, according to example embodiments of the present disclosure.

FIG. 9A is a flow diagram of an example method 900 for the creation of ordered sets of ephemeral emitter identification element values and a mapping of those ordered sets to specific system endpoints, according to example embodiments of the present disclosure. One or more portions of the example method 900 can be executed and/or implemented on one or more computing devices or computing systems. In addition, one or more portions of the example method 900 can be executed or implemented as an algorithm on the hardware devices or systems disclosed herein. FIG. 9A depicts steps performed in a particular order for purposes of illustration and discussion. As such, those skilled in the art, using the disclosures provided herein, will understand that various steps of any of the methods disclosed herein can be adapted, modified, rearranged, omitted, and/or expanded without deviating from the scope of the present disclosure.

In an embodiment, example method 900 can be used to assign ephemeral IDs to specific system endpoints. For example, assuming perfect timing and/or synchronization between the resolution entity and all system endpoint emitters, a necessary condition may be that there is at most one system endpoint emitter transmitting a given ephemeral ID element at a specific instant in time. Given the low scaling requirements relative to a large-scale beacon environment, synchronization issues may be avoided completely, for example, by using an assignment strategy that always maps a single ephemeral ID element value to a specific system endpoint emitter. In this way, situations can be avoided where, for example, due to imperfect synchronization, more than one system emitter could transmit the same ephemeral ID at the same time. In the present embodiment, the following can be assumed as an example illustration: (1) an ephemeral ID is 48 bits in length, (2) there are a maximum of 100,000 system emitters in a given AD deployment, (3) the ephemeral ID element changes every 3 minutes (i.e., 480 times a day), and (4) the nominal rollover period for the ephemeral ID assigned to a given system endpoint emitter is two months (28,800 different values per system endpoint). Similar to the pseudo-random element in Example Embodiment Two, the rollover period defines when the set of ephemeral ID element values for a given endpoint can be reused. The total number of unique ephemeral IDs needed are (100,000*28,800)=28,800,000,000 (which is approximately $2^{(34.74)}$) and, thus, this number can be represented by less than 35 bits. In this way, the total number of unique ephemeral IDs allocated for all the system emitters represents less than $\frac{1}{10,000}$ of the possible values of the 48-bit ephemeral ID numbering space.

In an example, method 900 performs operations associated with steps 901-907 to allocate ephemeral IDs to N specific system endpoint emitters. At Step 901, 28,800 unique values are randomly chosen from the set of values 0 through $(2^{(48)}-1)$. At Step 902, the set of values from Step 901 is labeled Ordered Set S1 and assigned to system endpoint emitter 1. The remaining ordered sets are labeled Si, where i ranges from 2 to N. The remaining ordered sets, Ordered Set S2 through Ordered Set SN, are iteratively formed by random choices of the remaining values not contained in prior ordered sets, for example, based on operations associated as depicted at Steps 903-Step 907 of method 900. Each of the Ordered Sets Si are assigned to a corresponding system endpoint emitter i (e.g., via configuration, during manufacture, etc.). This mapping of system endpoint emitter i to Ordered Set Si generally can be used in association with the ephemeral ID resolution process to be described shortly.

Figure 9B:
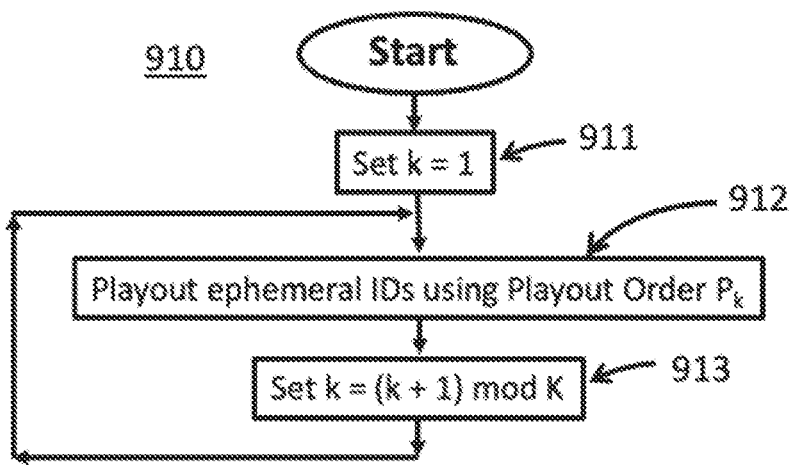
FIG. 9B is a flow diagram of an example method for the play out of a system endpoint's ordered set of ephemeral emitter identification element values via use of one of multiple play out lists for the system endpoint, according to example embodiments of the present disclosure.

FIG. 9B is a flow diagram of an example method 910 for the play out of a system endpoint's ordered set of ephemeral emitter identification element values via use of one of multiple play out lists for the system endpoint, according to example embodiments of the present disclosure. One or more portions of the example method 910 can be executed and/or implemented on one or more computing devices or computing systems. In addition, one or more portions of the example method 910 can be executed or implemented as an algorithm on the hardware devices or systems disclosed herein. FIG. 9B depicts steps performed in a particular order for purposes of illustration and discussion. As such, those skilled in the art, using the disclosures provided herein, will understand that various steps of any of the methods described herein can be adapted, modified, rearranged, omitted, and/or expanded without deviating from the scope of the present disclosure.

In an embodiment, example method 910 may be performed where ordered sets of values labeled Si (for system endpoint emitter i) of FIG. 9A are played out based on a specific order. For example, using the assumptions noted above, a given endpoint emitter i will play out 28,800 values over approximately two months. As such, in this embodiment, the next time Ordered Set Si is used by system endpoint emitter i, the values in this set will be output in a different order than the last time that the values in the set were output. This change of play out order is beneficial to help thwart malicious playback attacks as the new order is unpredictable. Each of the example play out orders defined below specifies the order in which elements in Ordered Set Si are output by a given system emitter i. In an example, method 910 creates K play out orders, labeled Pk where k ranges from 1 to K, with K being reasonably small (e.g., 10 or less). Also, the play out order elements should be randomized such that no two play out orders, Px and Py, are the same when x!=y. Further, keeping K reasonably small will limit the ephemeral ID resolution to reasonably small search possibilities.

In an embodiment, example method 910 performs operations of a process for choosing the play out order Pk. At Step 911, the index of the play out order, k, is set to 1. Upon the first execution of Step 912, the system endpoint emitter i begins to play out the ephemeral IDs in its ordered set (Ordered Set Si) via the play out order specified in Play Out Order P1. Upon exhaustion of all the ephemeral IDs in the Ordered Set Si, the next play out order is chosen to be the next higher play out order modulo K at Step 913. Then the play out order is incremented by one at each pass of the loop comprising Step 912 and Step 913, modulo K, and continues indefinitely. If K were 10, it would take approximately 20 months for the precise pattern of 10*28,800 ephemeral IDs to repeat (likely sufficiently long for protection against malicious endpoints). Ideally, each system endpoint i should store both the play out order index k (presently in use) and an index of where it currently is in that play out order in non-volatile memory, so that in the event of a power outage the respective system endpoint i can resume play back of the ephemeral IDs in the designed order, which is of benefit to the resolver.

In an embodiment, the mapping of ephemeral IDs to specific system endpoints generally may be referred to as the ephemeral ID to system endpoint resolution process. As each ephemeral ID to be resolved is unique to one of the Ordered Sets Si of the deployed system endpoints, a brute-force search could be made for the number of system endpoints in the AD. If Q is the number of system endpoints deployed in the AD, using the example numbers above would result in Q*28,800 valid ephemeral ID possibilities. However, after the system has been up for a while, the resolver can prioritize the search based on the recent history of ephemeral IDs from each endpoint. For example, if the resolver has seen a series of recent ephemeral IDs from a given system endpoint, it can determine the play out order Pk for that system endpoint at the recent time (e.g., Pk) by observing the sequence of ephemeral IDs (which have a unique series in each Pk). Based on knowing Pk from the past database records, the play out order at the current time (Pk or P(k+1) if near play out order rollover) can be estimated. Thus, the resolver can prioritize the search needed for the resolution based on the most likely values that it expects from all Q system endpoints. If a given system endpoint did not experience a power outage, then the resolver can limit the likely values to a small number (e.g., 10 or so). On the other hand, if the system endpoint did experience a power outage, then the resolver would need to consider a larger number of likely values. In this way, the resolver can prioritize the search. If the resolver can limit the search to 60 likely values or less (i.e., a span of 180 minutes of real time) on average per system endpoint, that would bring the search from a maximum of Q*28,800 tries down to Q*100 tries or less on average, resulting in a low-complexity resolution process.

Protection against replay attacks can be designed by ensuring the sequence of ephemeral IDs is what is expected from a given system endpoint emitter (by noting that the sequence is in a known and expected play out order). Good engineering should also guard against a potential denial-of-service attack of malicious endpoints reporting bogus ephemeral IDs to the ephemeral ID resolution service. When a received token with an ephemeral ID has been successfully resolved as expected (with no denial or service or replay attacks being encountered), the corresponding database record is marked as trusted, and the system emitter ID is associated with the record. A person skilled in the art can design an ephemeral ID resolution system similar to the above in a variety of ways.

In an embodiment, at some future time when a given user (e.g., "User A") tests positive for the disease, the process of notification may be similar or identical to example method 500 for performing contact tracing and notification. For example, trusted database records associated with received tokens may be used in association with the notification process while non-trusted records associated with received tokens can be excluded from such processing.

Persons skilled in the art will recognize that the embodiments associated with allocating ephemeral IDs to system endpoints in FIG. 9A and the embodiments associated with resolving/mapping ephemeral IDs from database reports to individual system endpoint emitters based on example method 910 of FIG. 9B are illustrative examples, and that a number of different ways are possible to obtain the same results. Further, Example Embodiment Three is an example where the tradeoffs have been made between complexity, privacy, and security for implementing the CT system described herein. As such, persons skilled in the art will recognized that other embodiments may consider different tradeoffs that result in different configurations and/or operations that achieve the same or substantially similar results of examples of the CT system described herein.

Example of a Federation of Administrative Domains

Figure 10:
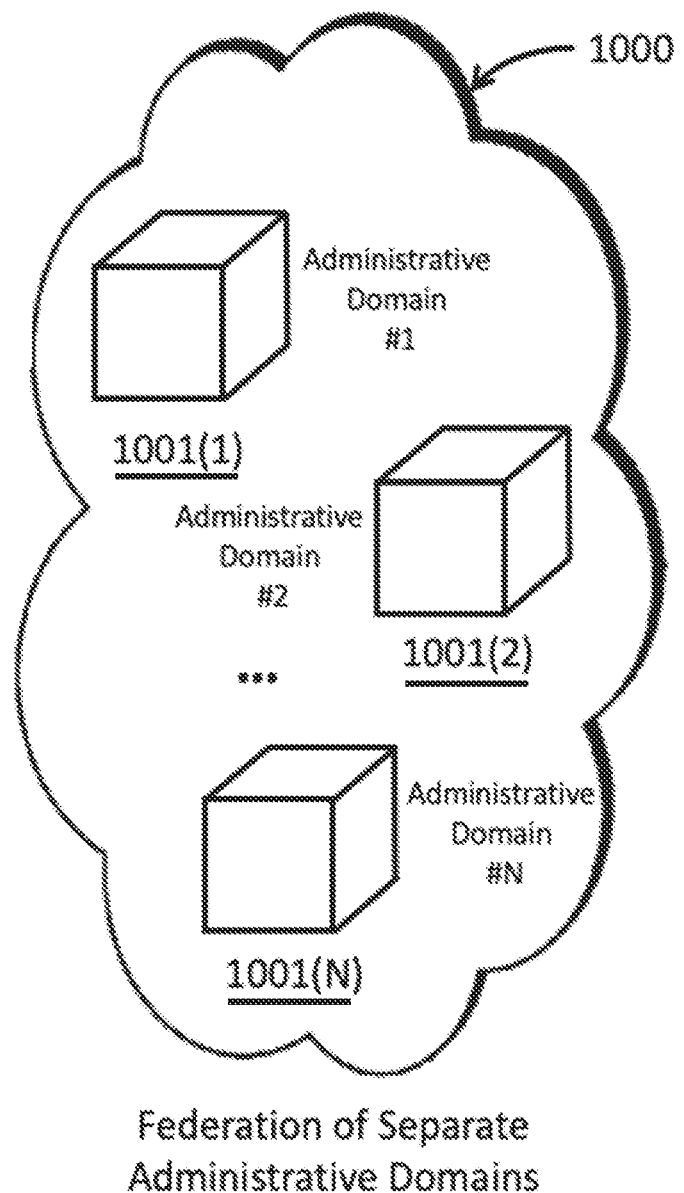
FIG. 10 is an illustration depicting an example of a federation of separate administrative domains, according to example embodiments of the present disclosure.

FIG. 10 depicts an example of a federation of ADs. System 1000 includes a federation of multiple ADs, labeled Administrative Domain 1001(1) through Administrative Domain 1001(N). In some embodiments, this configuration can exist, for example, when one or more ADs use compatible infrastructure (e.g., of the same manufacturer, compatible technology, etc.) and the entities controlling the respective ADs have a relationship by which using the information in the trusted and/or verified databases (e.g., elements of database records in databases such as Trusted Received Token Database 414, Trusted Received Token Database 614, Trusted Received Token Database 751, or Received Token Database 814) for each AD is consistent with their respective end-user permissions for sharing such information.

In an embodiment, information related to the received information tokens associated with a diseased person can be compared to information related to the received information tokens associated with other users in the same AD (e.g., same organization, same building, same campus, etc.) and/or in a federation of partnering ADs (e.g., another organization, another building of the same organization or a different organization, another campus of the same organization or a different organization, etc.).

Example Devices and Systems

Figure 11:
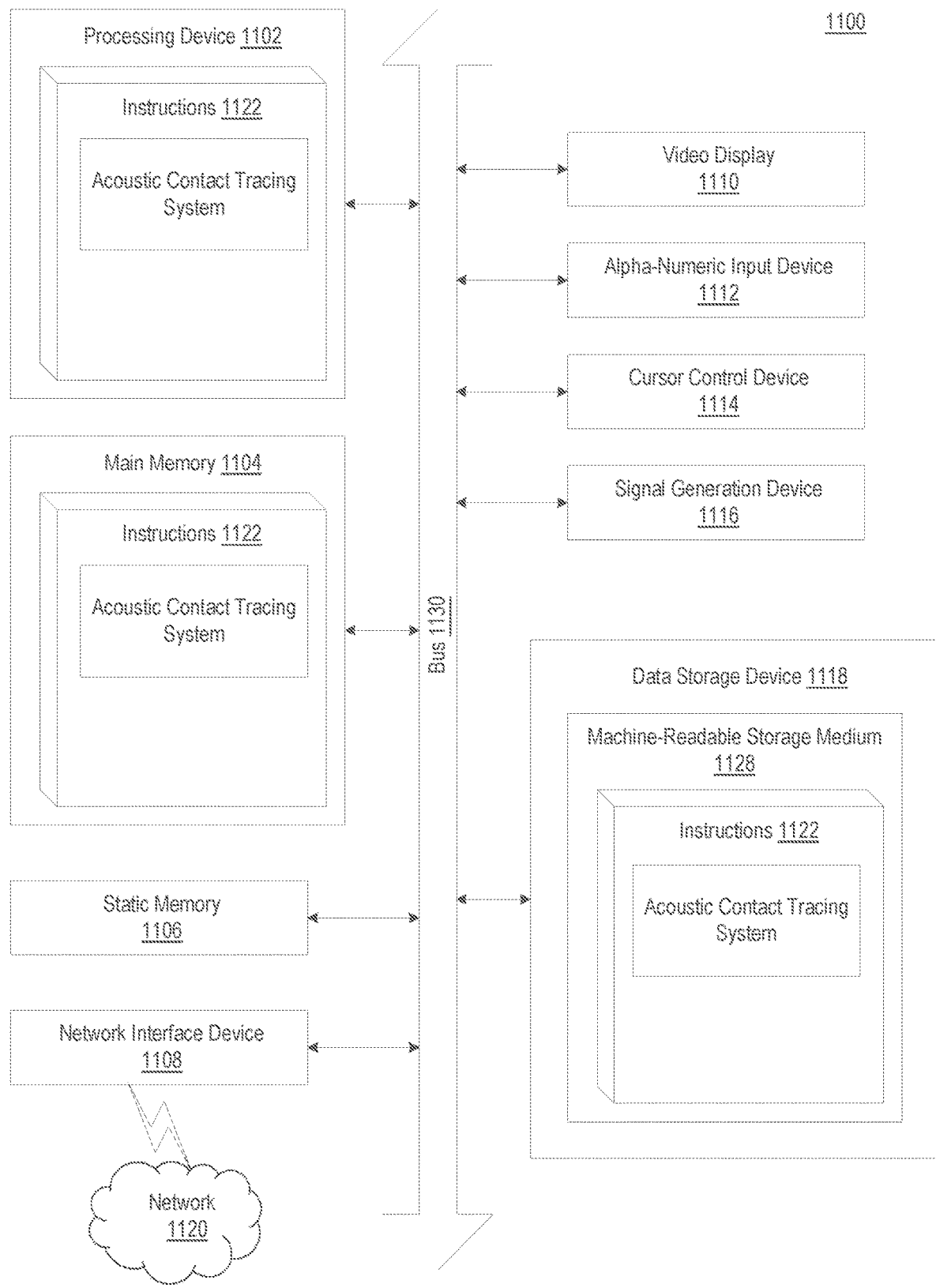
FIG. 11 depicts a block diagram of an example computer system that may perform one or more of the example embodiments of the present disclosure.

FIG. 11 illustrates a diagram of an example machine in the form of a computer system 1100, within which a set of instructions for causing the machine to perform any one or more of the operations discussed herein may be executed. In other examples, the machine may be connected (e.g., networked) to other machines in a LAN, an intranet, an extranet, or the interne. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a wearable computing device, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the operations discussed herein.

Computer system 1100 includes at least one processing device (e.g., processor 1102), a main memory 1104 (e.g., read-only memory (ROM), flash memory, dynamic random-access memory (DRAM) such as synchronous DRAM (SDRAM), double data rate (DDR SDRAM), or DRAM (RDRAM), etc.), a static memory 1106 (e.g., flash memory, static random-access memory (SRAM), etc.), and a data storage device 1118, which communicate with each other via a bus 1130.

Processor 1102 represents one or more processing devices such as a microprocessor, central processing unit, or the like. More particularly, the processor 1102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 1102 also may be one or more special-purpose processing devices such as an application specific integrated circuit (ASIC), a field programmable gate array (FPGA), a digital signal processor (DSP), network processor, or the like. The processor 1102 is configured to execute instructions 1122 for performing the operations associated with an acoustic contract tracing system as discussed herein.

The computer system 1100 also may include a network interface device 1108. The computer system 1100 may further include a video display unit 1110 (e.g., a liquid crystal display (LCD), a plasma display, etc.), an alphanumeric input device 1112 (e.g., a keyboard), a cursor control device 1114 (e.g., a mouse), and a signal generation device 1116 (e.g., a speaker).

The data storage device 1118 may include a computer-readable storage medium 1128 on which is stored one or more sets of instructions 1122 (e.g., software computer instructions) embodying any one or more of the examples described herein. The instructions 1122 also may reside, completely or at least partially, within the main memory 1104 and/or within the processor 1102 during execution thereof by the computer system 1100, the main memory 1104 and the processor 1102 also constituting computer-readable storage media. The instructions 1122 may be transmitted or received over a network 1120 via the network interface device 1108.

In one example, the instructions 1122 include instructions for one or more modules of an acoustic contact tracing system in accordance with examples of the present disclosure and/or a software library containing methods that call an acoustic contact tracing system in accordance with examples of the present disclosure. While the computer-readable storage medium 1128 (machine-readable storage medium) is shown as an example to be a single medium, the term "computer-readable storage medium" should be taken to include a single medium or multiple media (e.g., a centralized or distributed database, and/or associated caches and servers) that store the one or more sets of instructions. The term "computer-readable storage medium" also may include any medium that is capable of storing, encoding or carrying a set of instructions for execution by the machine and that cause the machine to perform any one or more of the operations of the present disclosure. The term "computer-readable storage medium" shall accordingly be taken to include, but not be limited to, solid-state memories, optical media, and magnetic media.

Numerous details are set forth in the foregoing description. However, it will be apparent to one skilled in the art having the benefit of this disclosure that the present disclosure may be practiced without these specific details. In some instances, well-known structures and devices are shown in block diagram form, rather than in detail, to avoid obscuring the present disclosure.

Some portions of the detailed description have been presented in terms of processes and symbolic representations of operations on data bits within a computer memory. Here, a process is generally conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "analyzing," "determining," "identifying," "adjusting," "transmitting," "receiving," "processing" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Certain examples of the present disclosure also relate to an apparatus for performing the operations herein. This apparatus may be constructed for the intended purposes, or it may comprise a computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

It is to be understood that the above description is intended to be illustrative, and not restrictive. Many other examples will be apparent to those of skill in the art upon reading and understanding the above description. The scope of the disclosure therefore should be determined with reference to the appended claims, along with the full scope of equivalents to which such claims are entitled.

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one skilled in the art. For instance, features illustrated or described as part of one embodiment can be used with another embodiment to yield a still further embodiment. Thus, it is intended that the present disclosure covers such alterations, variations, and equivalents.

What is claimed is:

1. A system for performing contact tracing based on acoustic communications, comprising:
    a first stand-alone emitter device that broadcasts acoustic tokens in an acoustic volume via an audio communication channel;
    one or more processor devices which are not a part of the emitter device, configured to:
        obtain, over a network, information associated with one or more acoustic tokens from a first user device of a first user, the one or more acoustic tokens being associated with the emitter device,
    obtain information associated with one or more acoustic tokens from a second user device of a second user, the one or more acoustic tokens being associated with the emitter device, and
        determine whether the second user was exposed to a disease associated with the first user in the acoustic volume based on analyzing the information associated with the one or more acoustic tokens from the first user device in view of the information associated with the one or more acoustic tokens from the second user device;
    wherein the emitter device is part of an administrative domain and broadcasts one or more acoustic tokens that each comprise a unique emitter device identification element associated with the emitter device; and
    wherein the system provides output information based on the determining of whether the second user was exposed to the disease associated with the first user in the acoustic volume.

2. The system of claim 1, wherein the outputting comprises:
    providing a notification to the second user indicating that the second user was exposed to the disease.

3. The system of claim 1, wherein the first emitter device is among a plurality of standalone emitter devices of an administrative domain and each of the emitter devices broadcasts one or more acoustic tokens that each comprise a unique emitter device identification element associated with a corresponding one of the emitter devices.

4. The system of claim 1, wherein at least one of the first user device or the second user device performs decoding of the one or more acoustic tokens associated with the emitter device.

5. The system of claim 1, wherein the one or more processor devices are further configured to:
    receive the information associated with the one or more acoustic tokens from the first user device; and
    store the information associated with the one or more acoustic tokens received from the first user device in a database.

6. The system of claim 1, wherein the one or more processor devices are further configured to:
    receive the information associated with the one or more acoustic tokens from the second user device; and
    store the information associated with the one or more acoustic tokens received from the second user device in a database.

7. The system of claim 1, wherein each of the acoustic tokens associated with the emitter device comprises a static emitter identification element.

8. The system of claim 1, wherein each of the one or more acoustic tokens associated with the emitter device comprise a static emitter identification element and a pseudorandom time element.

9. The system of claim 8, wherein the pseudo-random time element associated with each of the acoustic tokens is based on a corresponding result from a deterministic random word generator associated with the emitter device.

10. The system of claim 1, wherein each of the one or more acoustic tokens associated with the emitter device comprises an ephemeral emitter identification element.

11. The system of claim 10, wherein verification of each ephemeral emitter identification element is performed for determining whether information associated with a corresponding acoustic token is trusted.

12. The system of claim 10, wherein the emitter device plays out one or more ordered sets of ephemeral emitter identification elements across a plurality of acoustic tokens broadcast in the acoustic volume.

13. The system of claim 12, wherein each of the ephemeral emitter identification elements in the one or more ordered sets of ephemeral emitter identification elements corresponds only to the emitter device in view of one or more other emitter devices in a same administrative domain as the emitter device.

14. The system of claim 1, wherein the one or more processor devices are further configured to:
    receive information indicating that the first user tested positive for the disease.

15. The system of claim 1, wherein the information associated with the one or more acoustic tokens from the first user device is obtained based on a period of time associated with the disease.

16. The system of claim 1, wherein the information associated with the one or more acoustic tokens from the second user device is obtained based on a period of time associated with the disease.

17. The system of claim 1, wherein the determining that the first user was exposed to the disease is further based on information associated with radio frequency communication between the first user device and the second user device.

18. A computing system, comprising:
    a first stand-alone emitter device that broadcasts acoustic tokens in an acoustic volume via an audio communication channel;
    one or more processors which are not a part of the emitter device; and
    one or more non-transitory computer-readable media storing instructions that, when executed by the one or more processors, cause the one or more processors to:
        obtain, over a network, information associated with one or more acoustic tokens from a first user device of a first user, the one or more acoustic tokens being associated with an emitter device that broadcasts acoustic tokens in an acoustic volume via an audio communication channel;

obtain information associated with one or more acoustic tokens from a second user device of a second user, the one or more acoustic tokens being associated with the emitter device;

determine whether the second user was exposed to a disease associated with the first user in the acoustic volume based on analyzing the information associated with the one or more acoustic tokens from the first user device in view of the information associated with the one or more acoustic tokens from the second user device;

wherein the emitter device is part of an administrative domain and broadcasts one or more acoustic tokens that each comprise a unique emitter device identification element associated with the emitter device; and wherein the system provides a notification to the second user indicating that the second user was exposed to the disease based at least in part on determining that the second user was exposed to the first user in the acoustic volume.

19. A method comprising:

obtaining information associated with one or more acoustic tokens from a first user device of a first user, the one or more acoustic tokens being associated with an emitter device that broadcasts acoustic tokens via an audio communication channel;

obtaining information associated with one or more acoustic tokens from a second user device of a second user, the one or more acoustic tokens being associated with the emitter device;

determining whether the first user was exposed to a disease associated with the second user based on analyzing the information associated with the one or more acoustic tokens from the first user device in view of the information associated with the one or more acoustic tokens from the second user device; and outputting information based on determining whether the first user was exposed to the disease associated with the second user.

* * * * *